United States Patent
Kim et al.

(10) Patent No.: US 11,019,992 B2
(45) Date of Patent: Jun. 1, 2021

(54) EYESIGHT EXAMINATION METHOD, EYESIGHT EXAMINATION DEVICE, AND DOWNLOADER SERVER FOR STORING PROGRAM OF EYESIGHT EXAMINATION METHOD

(71) Applicant: VIEWMTECHNOLOGY CO. LTD., Gunpo-si (KR)

(72) Inventors: Ki Gon Kim, Seoul (KR); Kwang Kyu Lee, Seoul (KR)

(73) Assignee: VIEWMTECHNOLOGY CO. LTD., Gunpo-si (KR)

( * ) Notice: Subject to any disclaimer, the term of this patent is extended or adjusted under 35 U.S.C. 154(b) by 76 days.

(21) Appl. No.: 16/087,586

(22) PCT Filed: Mar. 15, 2017

(86) PCT No.: PCT/KR2017/002810
§ 371 (c)(1),
(2) Date: Sep. 21, 2018

(87) PCT Pub. No.: WO2017/164562
PCT Pub. Date: Sep. 28, 2017

(65) Prior Publication Data
US 2019/0104934 A1    Apr. 11, 2019

(30) Foreign Application Priority Data

Mar. 23, 2016 (KR) .................. 10-2016-0034443

(51) Int. Cl.
*A61B 3/032* (2006.01)
*A61B 3/00* (2006.01)

(52) U.S. Cl.
CPC .......... *A61B 3/032* (2013.01); *A61B 3/0058* (2013.01); *A61B 3/0025* (2013.01); *A61B 3/0033* (2013.01)

(58) Field of Classification Search
CPC ...................................................... A61B 3/032
See application file for complete search history.

(56) References Cited

U.S. PATENT DOCUMENTS 1,990,218 A * 2/1935 Bailey .................. A61B 3/02
351/244
4,714,330 A * 12/1987 Hennequin ............ A61B 3/032
351/237

(Continued)

FOREIGN PATENT DOCUMENTS

JP    06-237895 A    8/1994
JP    H08-038419 A   2/1996

(Continued)

OTHER PUBLICATIONS

TinyHands. "Raccoon Treehouse—Shape Matching Games App for Kids/Toddlers." YouTube, TinyHands, Mar. 19, 2016, www.youtube.com/watch?v=OyB1v0EQIbE (Year: 2016).*

(Continued)

*Primary Examiner* — Zachary W Wilkes
(74) *Attorney, Agent, or Firm* — Maschoff Brennan

(57) ABSTRACT

The present invention relates to an eyesight examination method, an eyesight examination device, and a downloader server for storing a program of the eyesight examination method, the eyesight examination method comprising the steps of: displaying an optotype image and a plurality of reference images; receiving a response to the optotype image; and determining whether a reference image determined on the basis of the response from among the plurality of reference images has the same shape as the optotype image, wherein one of the plurality of reference images has the same shape as the optotype image.

3 Claims, 7 Drawing Sheets

(56) References Cited

U.S. PATENT DOCUMENTS

| | | | | |
|---|---|---|---|---|
| 4,869,589 A * | 9/1989 | Blair | ................. | A61B 3/02 |
| | | | | 351/243 |
| 5,550,602 A * | 8/1996 | Braeuning | ............ | A61B 3/024 |
| | | | | 351/243 |
| 6,244,713 B1 * | 6/2001 | Hayashi | ................ | A61B 3/032 |
| | | | | 351/243 |
| 6,652,101 B1 * | 11/2003 | Glaser | ................... | A61B 3/032 |
| | | | | 351/239 |
| 6,808,267 B2 * | 10/2004 | O'Neil | ................... | G09B 7/00 |
| | | | | 351/223 |
| 8,087,781 B2 * | 1/2012 | Kanazawa | ........... | A61B 3/0033 |
| | | | | 351/222 |
| 8,888,288 B2 | 11/2014 | Iravani et al. | | |
| 8,894,209 B2 * | 11/2014 | Berry | ...................... | A61B 3/02 |
| | | | | 351/223 |
| 9,955,864 B2 * | 5/2018 | Rousseau | ................ | A61B 3/14 |
| 2012/0122066 A1 * | 5/2012 | Dohring | ................... | G09B 7/02 |
| | | | | 434/308 |
| 2017/0188810 A1 | 7/2017 | Kim et al. | | |

FOREIGN PATENT DOCUMENTS

| | | |
|---|---|---|
| JP | H09-224908 A | 9/1997 |
| KR | 10-2001-0100713 A | 11/2001 |
| KR | 101451669 B1 | 10/2014 |
| RU | 2010-126725 A | 1/2012 |

OTHER PUBLICATIONS

KR Office Action dated May 30, 2016 as received in Application No. 10-2016-0034443.

* cited by examiner

EYESIGHT EXAMINATION METHOD, EYESIGHT EXAMINATION DEVICE, AND DOWNLOADER SERVER FOR STORING PROGRAM OF EYESIGHT EXAMINATION METHOD

TECHNICAL FIELD

The present invention relates to an eyesight examination method, an eyesight examination device, and a downloader server for storing a program of an eyesight examination method and more specifically, to an eyesight examination method, an eyesight examination device, and a downloader server for storing a program of an eyesight examination method, capable of performing an eyesight examination automatically by simply using a user input and a variety of optotypes so as to precisely perform an eyesight examination for people of different age groups in a unified manner.

DESCRIPTION OF THE RELATED ART

An eyesight examination is performed at an ophthalmic clinic, an optician shop, in a medical check-up etc. In general, a subject is guided by an optician or a nurse so as to have an eyesight examination with a tool for covering one eye while looking at optotypes from a distance in an eyesight examination.

This applicant devised a new method for examining eyesight (Korean Patent No. 10-1451669 B1 published Oct. 17, 2014 and hereinafter referred to as "patent document 1") as a means to solve the problems with conventional methods for examining eyesight. The invention in patent document 1 is configured to automatically perform an eyesight examination through a user input with respect to two displayed figures by displaying the two figures expressed as lines.

The invention in patent document 1 is configured to receive a user selection (selection of direction) on the basis of the recognition of a distance between the lines of inside and outside figures. However, there are still problems with the invention in patent document 1.

An eyesight examination is performed through a selection of specific directions recognized on the basis of optotypes in terms of the Landolt optotypes or the optotypes of the invention in patent document 1 etc. However, those with astigmatism etc. have difficulty in specifying a direction exactly, thereby making it impossible to have an eyesight examination precisely.

Further, an eyesight examination is performed generally by using various types of optotypes (e.g. numbers, letters, Landolt Cs, ships, airplanes, umbrellas, animals). However, it is difficult to perform an eyesight examination precisely only with the Landolt optotypes or the optotypes of the invention in patent document 1.

When various types of optotypes are used for an eyesight examination, a subject needs to express opinions exactly. Accordingly, there is a need for a method of examining eyesight precisely only with simple expression of opinions.

Further, preferably, a subject needs to be able to express opinions without additional explanations through an intuitive input.

As a means to solve various problems with conventional methods of examining eyesight, provided are an eyesight examination method, an eyesight examination device, and a downloader server for storing a program of an eyesight examination method.

DETAILED DESCRIPTION OF THE INVENTION

Technical Problems

As a means to solve the above-described problems, provided are an eyesight examination method, an eyesight examination device, and a downloader server for storing a program of an eyesight examination method, capable of performing an eyesight examination automatically by using various types of optotypes.

Further, as a means to solve the above-described problems, provided are an eyesight examination method, an eyesight examination device, and a downloader server for storing a program of an eyesight examination method, capable of performing an eyesight examination precisely by enabling a selection of a response to various types of displayed optotypes regardless of refractive errors of eyes such as astigmatism etc.

Further, as a means to solve the above-described problems, provided are an eyesight examination method, an eyesight examination device, and a downloader server for storing a program of an eyesight examination method, capable of performing an eyesight examination automatically by enabling a subject of all age groups to make an intuitive selection of a response to displayed images without causing the subject to express opinions.

The technical problems to be solved by the present invention are not limited to the above-described ones, and other problems that have not been described may be clearly understood from the following description by one of ordinary skill in the art to which the present invention pertains.

Technical Solutions

An eyesight examination method performed by an eyesight examination device according to an aspect of the present invention includes (a) displaying an optotype image and a plurality of reference images, (b) receiving a response to the optotype image, and (c) determining whether of the plurality of reference images, a reference image determined through the response has the same shape as the optotype image, and one reference image among the plurality of reference images has the same shape as the optotype image.

According to the above-described eyesight examination method, each of the plurality of displayed reference images are positioned on the outskirts of the displayed optotype image in different directions, the response includes a direction input for selecting one reference image among a plurality of reference images, and the question whether a reference image corresponding to a direction input of the response and the optotype image have the same shape is determined in the step (c).

According to the above-described eyesight examination method, the reference image has a size the same as or larger than that of the largest of the optotype images having the same shape.

The above-described eyesight examination method further includes (d) displaying a following optotype image selected as a result of the determination made in the step (c) and a plurality of reference images, wherein two optotype images and two sets of a plurality of reference images positioned respectively on the outskirts of each of the optotype images are displayed in the steps (a) and (d) such that both eyes of a subject are examined.

An eyesight examination device according to an aspect of the present invention includes a display unit for displaying an optotype image and a plurality of reference images, an input unit for receiving a response to the optotype image, and a control unit for determining whether of the plurality of reference images, a reference image determined through the response has the same shape as the optotype image, and one reference image among the plurality of reference images has the same shape as the optotype image.

According to the above-described eyesight examination device, each of the plurality of reference images displayed onto the display unit are positioned on the outskirts of the optotype image in different directions, the response received through the input unit includes a direction input for selecting one reference image among a plurality of reference images, and the control unit determines whether of the plurality of reference images, a reference image corresponding to a direction input of the response and the optotype image have the same shape.

According to the above-described eyesight examination device, the control unit selects a following optotype image as a result of the determination on a determined reference image and an optotype image, outputs a selected following optotype image and a plurality of reference images through the display unit, and the display unit displays two optotype images and two sets of a plurality of reference images positioned respectively on the outskirts of each of the optotype images such that both eyes of a subject are examined.

According to the above-described eyesight examination device, the display unit includes two display modules for displaying each optotype image, and a reference optotype board for respectively displaying a plurality of reference images and for accommodating the two display modules.

According to the above-described eyesight examination device, the display unit includes two display modules for displaying each optotype image and a plurality of corresponding reference images, and the control unit configures a plurality of reference images to respectively have a size the same as or larger than that of the largest of optotype images having the same shape so as to output each of the plurality of reference images together with an optotype image onto the display modules.

A downloader server for storing a program of an eyesight examination method, according to one aspect of the present invention, includes a communication module for receiving a download request through a network and transmitting a program corresponding to the download request through a network, a storage module configured to store a plurality of programs and to store an eyesight examination program for executing the eyesight examination method, and a control module for delivering the eyesight examination program stored in the storage module to the communication module according to the request for downloading an eyesight examination program, which is received through the communication module.

Advantageous Effects

An eyesight examination method, an eyesight examination device, and a downloader server for storing a program of an eyesight examination method, according to the present invention, have the advantage of performing an eyesight examination automatically by using various types of optotypes.

Further, an eyesight examination method, an eyesight examination device, and a downloader server for storing a program of an eyesight examination method, according to the present invention, have the advantage of performing an eyesight examination precisely by enabling a selection of a response to various types of displayed optotypes regardless of refractive errors of eyes such as astigmatism etc.

Further, an eyesight examination method, an eyesight examination device, and a downloader server for storing a program of an eyesight examination method, according to the present invention, have the advantage of performing an eyesight examination automatically by enabling a subject of all age groups to make an intuitive selection of a response to displayed images without causing the subject to express opinions.

The advantages to be achieved by the present invention are not limited to the above-described ones, and other advantages that have not been described may be clearly understood from the following description by one of ordinary skill in the art to which the present invention pertains.

DESCRIPTION OF THE SYMBOLS

Figure 1:
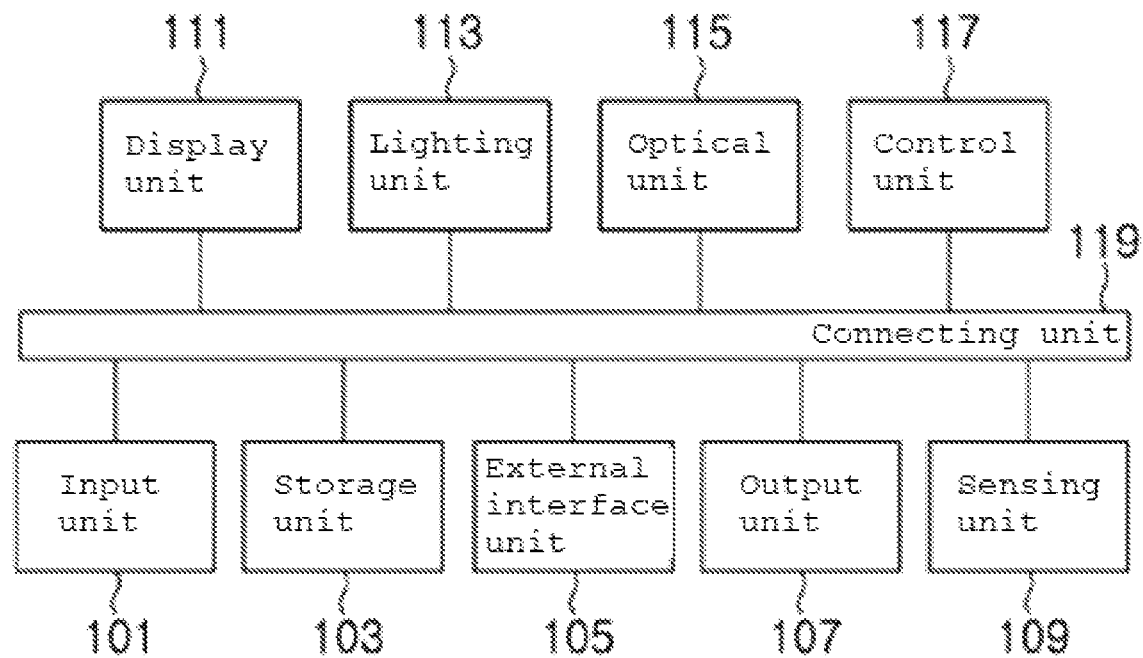
FIG. 1 illustrates an exemplary block diagram of an eyesight examination device.

100: Eyesight examination device
101: Input unit 103: Storage unit
105: External interface unit 107: Output unit
109: Sensing unit 111: Display unit
111-1: Display module 111-3: Reference optotype board
113: Lighting unit 115: Optical unit
117: Control unit 119: Connecting unit Mode for Carrying Out the Invention The above-described objects, features, and advantages of the present invention will become apparent from the following detailed description that will be provided with reference to the attached drawings. Accordingly, those skilled in the art to which the present invention pertains can easily embody the present invention. Further, in describing the present invention, detailed descriptions of the known technology in relation to the present invention will be omitted if they are deemed to make the gist of the present invention unnecessarily vague. Below, preferred embodiments of the present invention will be described in detail with reference to the attached drawings.

FIG. 1 illustrates an exemplary block diagram of an eyesight examination device 100.

According to FIG. 1, an eyesight examination device 100 includes an input unit 101, a storage unit 103, an external interface unit 105, an output unit 107, a sensing unit 109, a display unit 111, a lighting unit 113, an optical unit 115, a control unit 117 and a connecting unit 119.

The blocks included in FIG. 1 may be omitted depending on the type of an eyesight examination device 100 or examples of changes in the design of an eyesight examination device 100, and blocks that are not included in FIG. 1 may be further included in the block diagram.

Figure 2:
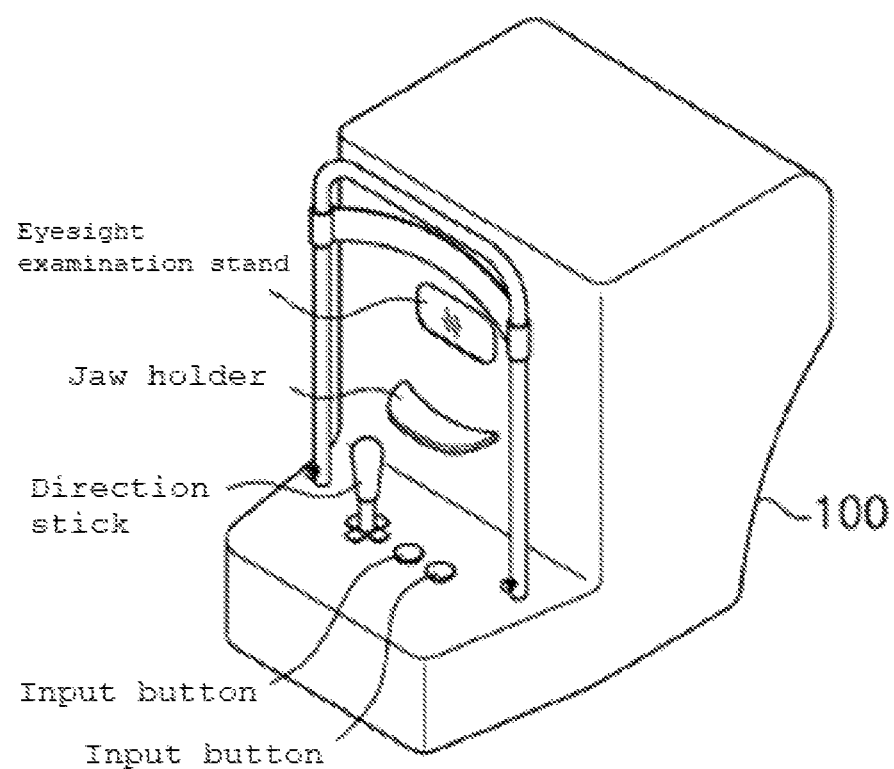
FIG. 2 illustrates an exemplary appearance of an eyesight examination device.

Various kinds of devices may be used as the eyesight examination device 100. For instance, the eyesight examination device 100 may be configured as a mobile phone, a smart phone, a tablet PC etc., or a personal computer (PC) etc., or a server that is capable of performing an eyesight examination by connecting a network such as the Internet etc., or a terminal exclusive for an eyesight examination (ref. FIG. 2).

Depending on the type of an eyesight examination device 100, specific blocks may be omitted. For instance, if a PC, a smart phone, a tablet PC etc. are used as the eyesight examination device 100, a lighting unit 113, an optical unit 115, and/or a sensing unit 109 etc. may be omitted depending on examples of the configuration of each device.

Suppose that a terminal exclusive for an eyesight examination is used as the eyesight examination device 100, and take a look at each block of the eyesight examination device 100 in FIG. 1. The input unit 101 receives a user input from a subject. The input unit 101 is provided with a direction stick 101*a* for choosing direction 2, direction 4, or direction 8, one or more buttons 101*b*, a touch panel 101*c*, a touch pad 101*d*, a mouse 101*e*, a keyboard 101*f* etc. so as to receive a user input and to output the same into the control unit 117.

The user input received by the input unit 101 may show a response to an optotype image displayed for an eyesight examination. For instance, the response to an optotype image may include a direction input showing a direction from an optotype image to a selected reference image so as to select one reference image among a plurality of reference images displayed together with an optotype image. The response may show a direction input itself or a signal for extracting a direction input.

The input unit 101 may be used to enable the other user to control the eyesight examination device 100. For instance, the input unit 101 receives a user input for requesting the drive of the eyesight examination device 100, the start, finish of an eyesight examination program of the eyesight examination device 100, the output of eyesight examination results etc., and transmits the user request into the control unit 117.

The storage unit 103 stores a variety of data and programs. The storage unit 103 includes a mass storage medium such as volatile memory, non-volatile memory and/or a hard disk etc. For instance, the storage unit 103 stores an eyesight examination program used for an eyesight examination. The eyesight examination program may be downloaded form a downloader server through a network. The eyesight examination program is loaded onto the control unit 117 and performs an eyesight examination of a user (subject) so as to generate eyesight examination results and to output the same.

Additionally, the storage unit 103 stores a variety of data used for an eyesight examination. For instance, the storage unit may store a plurality of optotype image groups used for eyesight examinations. Each optotype image group includes different optotype image groups with respect to the same shape. For instance, one optotype image group includes Landolt optotype images of different sizes, and another optotype image group may be used for an eyesight examination and include optotype images showing specific numbers, specific letters, specific pictures (e.g. umbrella, ship, airplane etc.) etc. having the same shape. Yet another optotype image group includes optotype images showing numbers, letters, pictures etc., which have shapes different from those of the above-described optotype images. As described above, the optotype image groups include optotype images having the same shapes with different sizes.

The optotype image groups include a plurality of optotype images of different sizes and reference images having the same shapes as the optotype images. Each optotype image corresponds to specific eyesight data (visual acuity values, e.g. 0.1, 0.2, 2.0 etc.). The reference image has the same shape as the optotype image and has a size the same as or larger than that of the largest of the optotype images. The reference images may be displayed and used for a response made by a user.

As with the display unit 111 in FIGS. 1 to 3, which will be described on the basis of various configurations, the optotype image groups may be cut (carved, drawn) in advance on the display unit 111, rather than stored in the storage unit 103, and an optotype image of a specific optotype image group and a reference image of a specific optotype image group among one or more optotype image groups may be shown according to a control signal of the control unit 117.

The external interface unit 105 is configured as an interface for connecting with a device outside the eyesight examination device 100. The external interface unit 105 may perform short-range communication so as to connect with a remote control, a fax, a PC etc. The external interface unit 105 is provided with an interface for the signals of an infrared remote control, ethernet, bluetooth, or a communication interface for a fax etc. so as to transmit or output eyesight examination results according to the control by the control unit 117. Further, the external interface 105 receives control data from an external device so as to transmit the same to the control unit 117. The control unit 117 may perform operations according to the received control data.

The output unit 107 outputs eyesight examination results generated by the control unit 117. The output unit 107 includes a display module such as a liquid-crystal display (LCD), a light-emitting diode (LED) etc., a printer module that may be built into the case of the eyesight examination device 100, and/or an interface for connecting with an external printer.

The output unit 107 may further include a speaker. The speaker may output a voice for notifying eyesight examination results, and a guide speech for announcing the start of an eyesight examination or leading a subject (user) to make a move or an action according to the control by the control unit 117.

The sensing unit 109 recognizes a subject or user of an eyesight examination. The control unit 117 may start an eyesight examination according to the recognition of a subject by the sensing unit 109. The sensing unit 109 may include a pressure sensor for sensing pressure applied to a jaw holder, a temperature sensor for sensing the body temperature of a subject or a user sensed at an eyesight examination stand, an infrared sensor for recognizing a subject or a user, a proximity sensor for sensing the proximity of a subject or a user, and/or a circuit for outputting signals changed according to pressure applied to the jaw holder etc.

Herein, the subject or the user may be interchangeably used throughout the specification. More strictly, a person who is taking an eyesight examination according to the guide of another person is recognized as a subject, and a person who performs an eyesight examination according to the will of a person using the eyesight examination device 100 may be recognized as a user. Below, two types of users all will be referred to as a subject.

Signals sensed by the sensing unit 109 are output into the control unit 117, and the control unit 117 may start an eyesight examination, load an eyesight examination program or provide guides to a subject depending on the type of an eyesight examination device 100.

The display unit 111 displays images. The display unit 111 includes one or more display modules 111-1, and preferably includes two display modules 111-1.

If the display unit 111 consists of two display modules 111-1, one display module 111-1 (hereinafter referred to as "left eye display module") displays an image for examining the eyesight of the left eye (hereinafter referred to as "left eye"), and the other display module 111-1 (hereinafter referred to as "right eye display module") displays an image for examining the eyesight of the right eye (hereinafter referred to as "right eye").

The left eye display module 111-1 is used to examine the eyesight of the left eye, the right eye display module 111-1 is used to examine the eyesight of the right eye, and the two display modules 111-1 are all used to examine the eyesight of both eyes. The relative positions of the left eye display module 111-1 and the right eye display module 111-1 inside the eyesight examination device 100 may be changed depending on the lens of the optical unit 115 and/or the structure of a reflecting mirror etc.

The display unit 111 may consist of a single display module 111-1. In this case, the single display module 111-1 may be used to examine the eyesight of the left eye, the right eye, and/or both eyes.

The display module 111-1 may be an LCD module or an LED module. Each display module 111-1 receives images or video signals from the control unit 117 through a promised interface, and displays images (video) according to the received signals.

The display module 111-1 may be a graphic pixel-type LCD module. In the case of a graphic pixel-type LCD module, the size of the pixel of the LCD module is preferably configured to be no more than 0.04 mm. If the size of the graphic pixel is configured to be no more than 0.04 mm, the range of eyesight examination results (e.g. 1 to 2.0) may be covered and eyesight may be tested.

The display module 111-1 may be a segment-type LCD module. The segment-type LCD module may show precise optotypes (images) used for an eyesight examination because specific patterns, shapes used as optotype images for an eyesight examination are drawn (carved) in advance. The segment-type LCD module is configured to draw optotype images of one optotype image group or a plurality of optotype image groups in advance, and to show a specific optotype image according to the control by the control unit 117. For instance, the segment-type LCD module may highlight a specific optotype image by means of a control signal of the control unit 117 for displaying a specific optotype image, and may display (highlight) another specific optotype image by means of another control signal of the control unit 117.

Figure 3:
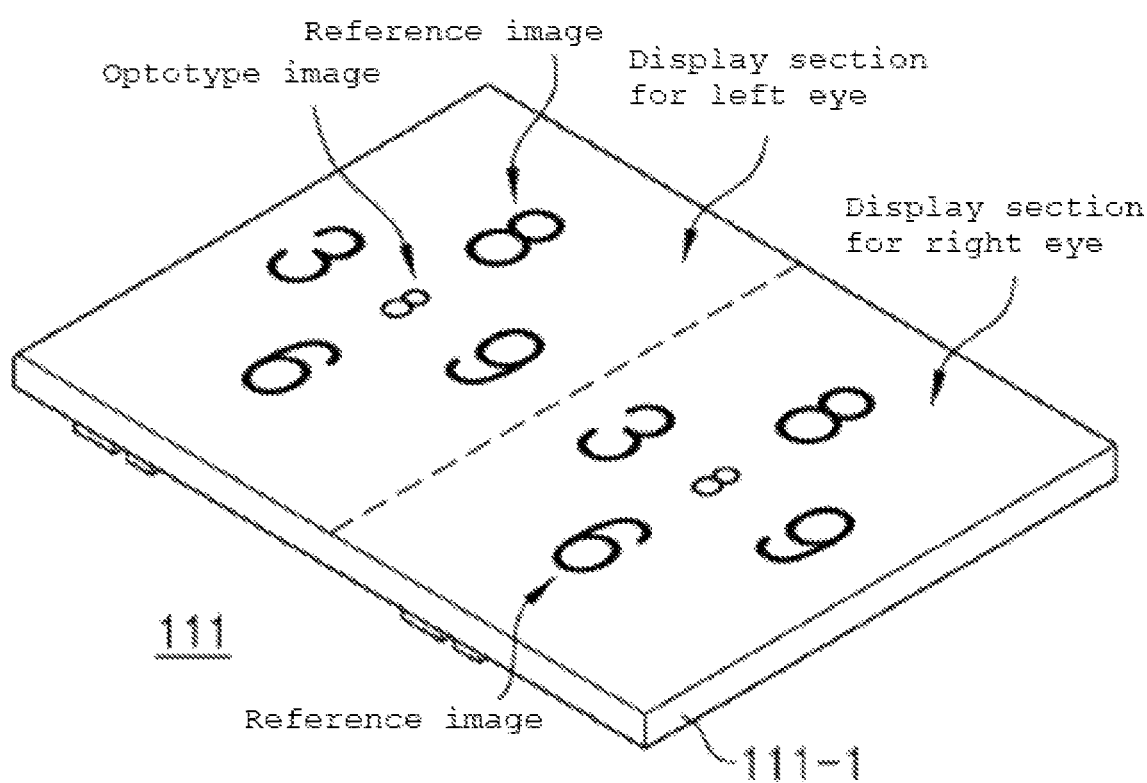
FIG. 3 illustrates a display unit consisting of a single graphic pixel-type display module.
Figure 4:
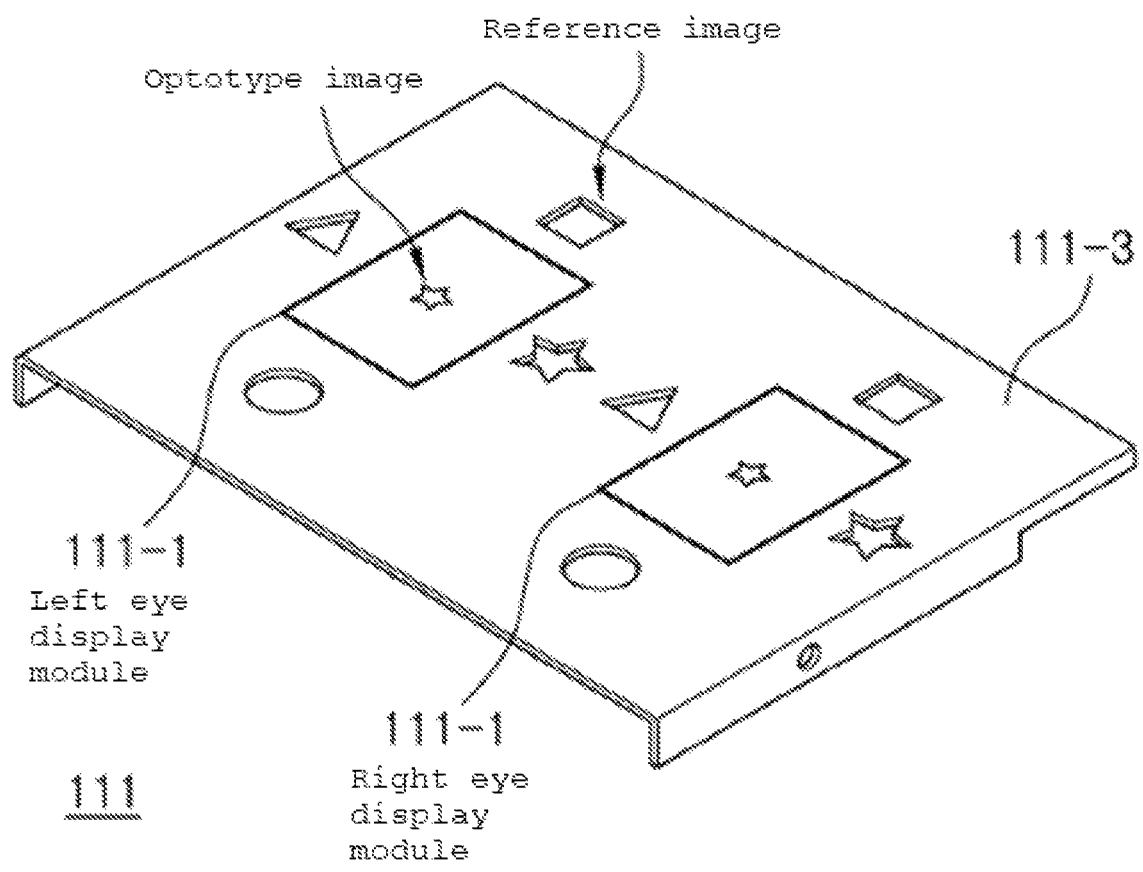
FIG. 4 illustrates a display unit consisting of two graphic pixel-type display modules.
Figure 5:
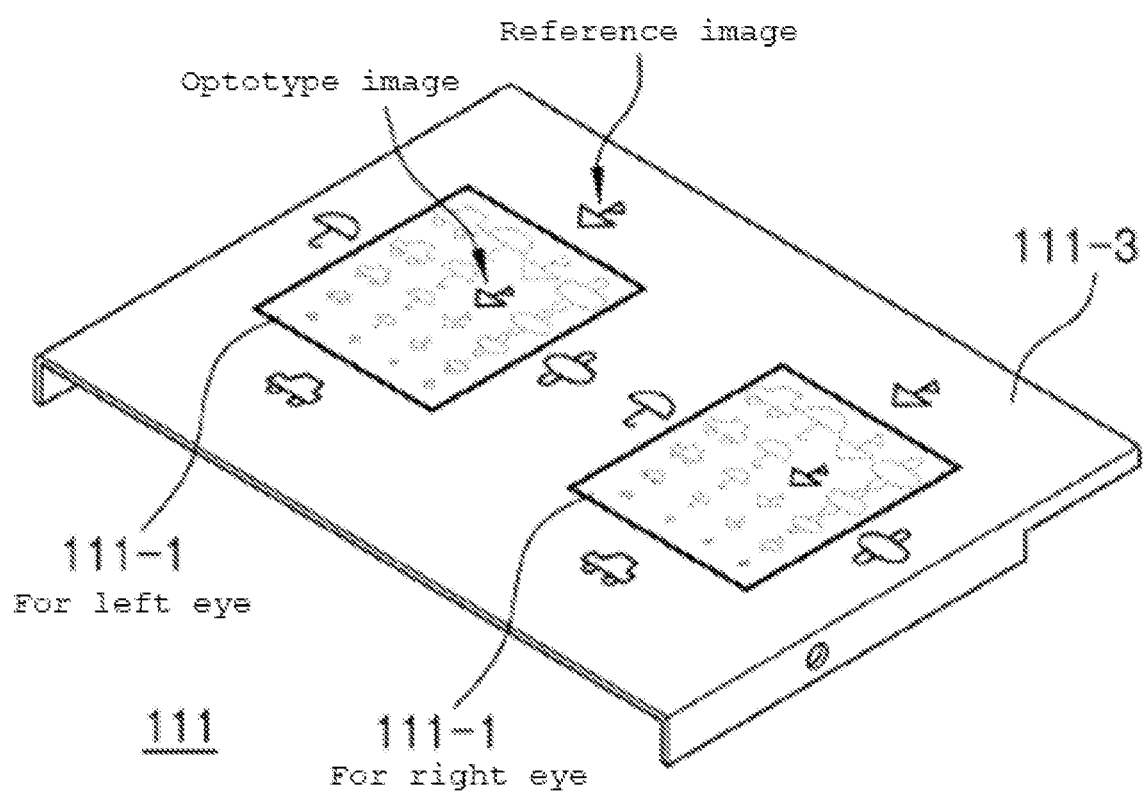
FIG. 5 illustrates a display unit consisting of a segment-type display module.

FIGS. 3 to 5 illustrate the configurations of various types of display units 111.

FIG. 3 illustrates a display unit 111 consisting of a single graphic pixel-type display module 111-1, FIG. 4 illustrates a display unit 111 consisting of two graphic pixel-type display modules 111-1, and FIG. 5 illustrates a display unit 111 consisting of a segment-type display module 111-1.

As illustrated in FIGS. 3 to 5, the display unit 111 displays an optotype image used for the current eyesight examination and a plurality of reference images used for generating a response to the optotype image from a subject.

Optotype images are selected from optotype image groups (in the storage unit 103 or drawn in advance) by the control unit 117, and reference images are positioned on the outskirts of an optotype image. For instance, one reference image of two reference images may be positioned on the left of an optotype image, and the other reference image may be positioned on the right of the optotype image. For instance, one reference image of four reference images may be positioned on the left of an optotype image, and another reference image may be positioned on the right of the optotype image, another reference image may be positioned on the lower side of the optotype image, and the other reference image may be positioned on the upper side of the optotype image.

One of the displayed reference images has the same shape as the optotype image that is currently displayed. That is, one of the reference images has the same shape as the displayed optotype image, and the other reference images are configured to have a different shape from the optotype image that is currently displayed.

As illustrated in FIG. 3, the display unit 111 consists of a single display module 111-1, and the display module 111-1 may be a graphic pixel LCD module or a graphic pixel LED module. In this case, the display module 111-1 may be divided into two sections. One display section may be for examining the eyesight of the left eye, and the other display section may be for examining the eyesight of the right eye. The two display sections are used simultaneously for examining the eyesight of both eyes (ref. FIG. 3).

At the time of examining the eyesight of both eyes, an optotype image and a plurality of reference images (direction or direction 4) displayed in the display section for the left eye, and an optotype image and a plurality of reference images displayed in the display section for the right eye are the same.

As illustrated in FIG. 4 as another configuration example, the display unit 111 consists of two display modules 111-1, and each display module 111-1 may be a graphic pixel LCD module or a graphic pixel LED module.

One display module 111-1 is used as a display module for the left eye 111-1, which displays an optotype image at the time of examining the eyesight of the left eye, and the other display module 111-1 is used as a display module for the right eye 111-1, which displays an optotype image at the time of examining the eyesight of the right eye. The display unit 111 is configured to display the same optotype image on the two display modules 111-1 so as to examine the eyesight of both eyes.

The display unit 111 in FIG. 4 may further include a reference optotype board 111-3. The reference optotype board 111-3 may accommodate two display modules 111-1. That is, the reference optotype board 111-3 may be coupled through the holes provided to the two display modules 111-1 and may be separated. Another reference optotype board 111-3 may be coupled to the display unit 111 or to the eyesight examination device 100. A reference optotype board 111-3 may include two holes (rectangular holes) capable of accommodating two display modules 111-1 and may be coupled to or separated from the display module 111-1 through the two holes. The reference optotype board 111-3 may be fixed to and separated from the inside of the eyesight examination device 100 through a coupling means (e.g. screws, adhesive materials, mechanical structures for coupling etc.).

The reference optotype board 111-3 may display a plurality of reference images. As illustrated in FIG. 4, the reference optotype board 111-3 may display reference images in the upward, downward, left and right directions of each display module 111-1. Reference images are printed on the reference optotype board 111-3 or carved on the reference optotype board 111-3 through hollow relief or relief such that the reference images are shown. In this case, the reference images are recognized by a subject through an LED light etc. at the time of examining the eyesight.

The reference optotype board 111-3 may be omitted depending on the size of a display module 111-1 or changes in the design of a display module 111-1, or each display module 111-1 may display all the reference images positioned on the outskirts of the optotype image.

As illustrated in FIG. 5 as another configuration example, the display unit 111 includes two display modules 111-1 and a reference optotype board 111-3. Each display module 111-1 is a segment-type LCD module.

One display module 111-1 is used as a display module for the left eye 111-1, which displays an optotype image at the time of examining the eyesight of the left eye, and the other display module 111-1 is used as a display module for the right eye 111-1, which displays an optotype image at the time of examining the eyesight of the right eye. The display unit 111 is configured to display an optotype image on the two display modules 111-1 so as to examine the eyesight of both eyes.

The segment LCD module may draw (carve) all the optotype images of one or more optotype image groups in advance, and display one specific optotype image according to the control signal selected by the control unit 117. For instance, when the control unit 117 outputs a control signal for supplying power to a selected optotype image, the segment LCD module may display the selected optotype image.

The display unit 111 in FIG. 5 may further include a reference optotype board 111-3, and the reference optotype board 111-3 is configured to accommodate two display modules 111-1. Each display module 111-1 may be coupled to the reference optotype board 111-3 through the holes etc. (e.g. rectangular holes) provided to the two display modules 111-1 and may be separated. Another reference optotype board 111-3 displaying other reference images may be coupled to the display unit 111 or to the eyesight examination device 100. A reference optotype board 111-3 may be fixed to and separated from the inside of the eyesight examination device 100 through a coupling means (e.g. screws, adhesive materials, mechanical structures for coupling etc.).

The reference optotype board 111-3 may display a plurality of reference images. As illustrated in FIG. 4 or 5, the reference optotype board 111-3 may display reference images in the upward, downward, left and right directions of each display module 111-1. Reference images are printed on the reference optotype board 111-3 or expressed through hollow relief or relief. In this case, the reference images are recognized by a subject through an LED light etc. at the time of examining the eyesight.

The two segment LCD modules in FIG. 5 may be coupled to or separated from the eyesight examination device 100. For instance, the two segment LCD modules are replaced with a segment LCD display module capable of displaying optotype images of another optotype image group depending, if necessary, such that the replaced segment LCD display module is installed in the eyesight examination device 100.

As illustrated in FIGS. 3 to 5 as various configuration examples, the display unit 111 displays optotype images used for examining eyesight according to the control by the control unit 117 and displays a plurality of reference images. (Only) one reference image of the plurality of reference images has the same shape as the optotype image that is currently displayed. For instance, if the optotype image is number 8, an umbrella, a ship, an airplane, one of the plurality reference images is number 8, an umbrella, a ship, an airplane that are the same as the optotype image.

The reference images have the same size as the largest of the optotype images having the same shape or a size larger than that of the largest of the optotype images having the same shape, or a subject recognizes that a displayed reference image has the same size as the largest of the optotype images or a size larger than that of the largest of the optotype images.

Take a look at the blocks in FIG. 1 again. The lighting unit 113 outputs light onto the display unit 111. The lighting unit 113 includes a plurality of white LEDs or color LEDs so as to keep the optotype images and reference images displayed on the display modules 111-1 of the display unit 111 at a constant light level.

Take a closer look at an exemplary configuration of the lighting unit 113 with respect to the display unit 111. If the display unit 111 includes a reference optotype board 111-3, the lighting unit 113 includes a plurality of LEDs so as to light reference images of the reference optotype board 111-3. One or more LEDs among the plurality of LEDs lighting the reference optotype board 111-3 light reference images on the left eye side of the reference optotype board 111-3 and are controlled by the control unit 117. Another or more LEDs among the plurality of LEDs lighting the reference optotype board 111-3 light reference images on the right eye side of the reference optotype board 111-3 and are controlled according to the control signal of the control unit 117. Further, the lighting unit 113 includes one or more LEDs so as to light each display module 111-1. If display modules themselves include LEDs, LEDs for lighting display modules 111-1 may be omitted.

The optical unit 115 includes one or more lenses and reflecting mirrors so as to enable the eyes of a subject to recognize an optotype image and a plurality of reference images of the display unit 111 inside the eyesight examination device 100. The optical unit 115 may be omitted depending on the type of an eyesight examination device 100.

The control unit 117 controls each block of the eyesight examination device 100. The control unit 117 uses an eyesight examination program and data (e.g. an optotype image etc.) that are stored in the storage unit 103 so as to process data according to the program and to control other blocks.

The control unit 117 reacts and processes data according to the input performed by a subject or by a manager of the eyesight examination device 100 through the input unit 101 so as to output the results of processing the data through the output unit 107. The control unit 117 includes one or more execution units for executing a program code, and may mean or may be referred to as a processor, a microcomputer, a central processing unit (CPU), a microprocessing unit (MPU) etc.

The control unit 117 may load an eyesight examination program according to the input received through the input unit 101, sets an eyesight examination mode with respect to both eyes, the left eye and/or the right eye of a subject within the eyesight examination program, and performs an eyesight examination in a mode designated as a subject recognition through a sensing unit 109.

At the time of examining the left eye, the control unit 117 controls the left eye display module 111-1 and the reference optotype board 111-3 so as display an optotype image and a plurality of reference images. At the time of examining the right eye, the control unit 117 controls the right eye display module 111-1 and the reference optotype board 111-3 so as display an optotype image and a plurality of reference images. At the time of examining both eyes, the control unit 117 controls the right eye and left eye display modules 111-1 and the reference optotype board 111-3 so as display each optotype image and each of the plurality of reference images.

After displaying an optotype image, the control unit 117 may receive a response of a subject through the input unit 101 during the process of an eyesight examination. A subject inputs a response to an optotype image through the input unit 101 according to the recognition of the displayed optotype image and the displayed plurality of reference images, and the input unit 101 receives an input signal representing a response.

For instance, a subject may recognize a reference image having the same shape as an optotype image, and input a response representing a direction from the optotype image to the reference image having the same shape as the optotype image through a direction stick or a button etc. The input unit 101 receives a signal representing the response from the direction stick or the button etc.

According to the receipt of a response, the control unit 117 determines a reference image selected from the plurality of displayed reference images on the basis of the response and determines whether the determined reference image has the same shape as the optotype image that is currently displayed.

For instance, the control unit 117 receives a direction input through the input unit 101, determines a reference image corresponding to the direction input among a plurality of reference images of direction 2, direction 4, direction 8, and determines whether the determined reference image is the same as the optotype image that is currently displayed. The control unit 117 may determine a direction of a reference image having the same shape as an optotype image that is currently displayed, in advance, depending on whether a direction input is the same as a direction determined in advance.

The control unit 117 determines a following optotype image as a result of determining whether a reference image is the same as an optotype image that is currently displayed. For instance, when determining that a reference image is the same as an optotype image that is currently displayed, the control unit 117 may select an optotype image having a visual acuity value smaller than that corresponding to an optotype image that is currently displayed. If the control unit determines that a reference image is different from an optotype image that is currently displayed, the control unit 117 may select an optotype image having a visual acuity value larger than that corresponding to an optotype image that is currently displayed. A selected optotype image may be the same as or different from an optotype image that is currently displayed.

Further, according to the selection of a following optotype image, the control unit 117 may determine a plurality of reference images that will be used for the following optotype image. The determination of reference images may be omitted according to a configuration example (e.g. reference optotype board 111-3) of a display unit 111.

According to the determination of a following optotype image and a plurality of reference images, the control unit 117 outputs an image (video) signal representing a following optotype image and a plurality of reference images into the display unit 111.

At the time of examining one eye (e.g. the left eye or the right eye), the control unit 117 outputs a single optotype image and a plurality of reference images positioned on the outskirts of the optotype image through the display unit 111. At the time of examining both eyes, the control unit 117 outputs two optotype images and a plurality of reference images positioned on the outskirts of each of the optotype images through the display unit 111.

The connecting unit 119 receives and transmits data and control data among blocks. The connecting unit consists of a combination of one or more a parallel bus, a serial bus, a general-purpose input/output (GPIO) etc.

FIG. 2 illustrates an exemplary appearance of an eyesight examination device 100.

The eyesight examination device 100 in FIG. 2 is an example of a terminal exclusive for an eyesight examination configured according to the present invention. According to FIG. 2, the eyesight examination device 100 includes a jaw holder and an eyesight examination stand, and includes a direction stick and one or more buttons that are included in the input unit 101. The direction stick or one specific button may be omitted or replaced with another input means performing identical or similar functions according to a modified example.

Take a brief look at the appearance of the eyesight examination device 100. The jaw holder is a device for holding the jaw of a face at the time of examining eyesight, and the eyesight examination stand is configured to accommodate both eyes such that an image exposed to one eye or both eyes is displayed through the eyesight examination stand.

The direction stick is configured to direct a specific direction representing a reference image the same as an optotype image displayed through the eyesight examination stand. For instance, the direction stick outputs a direction signal representing the upward, downward, left and right directions into the control unit 117 of the eyesight examination device 100.

The button is also used to input a reaction (response) of a subject with respect to a displayed optotype image. For instance, if a subject cannot recognize an optotype image or cannot find a reference image the same as the optotype image, the button may be used to show it.

The button, the direction stick or both thereof may be used for an eyesight examination. The button or the direction stick may be omitted according to the use of an eyesight examination. The button is a push-type one or a touch-type one.

Figure 6:
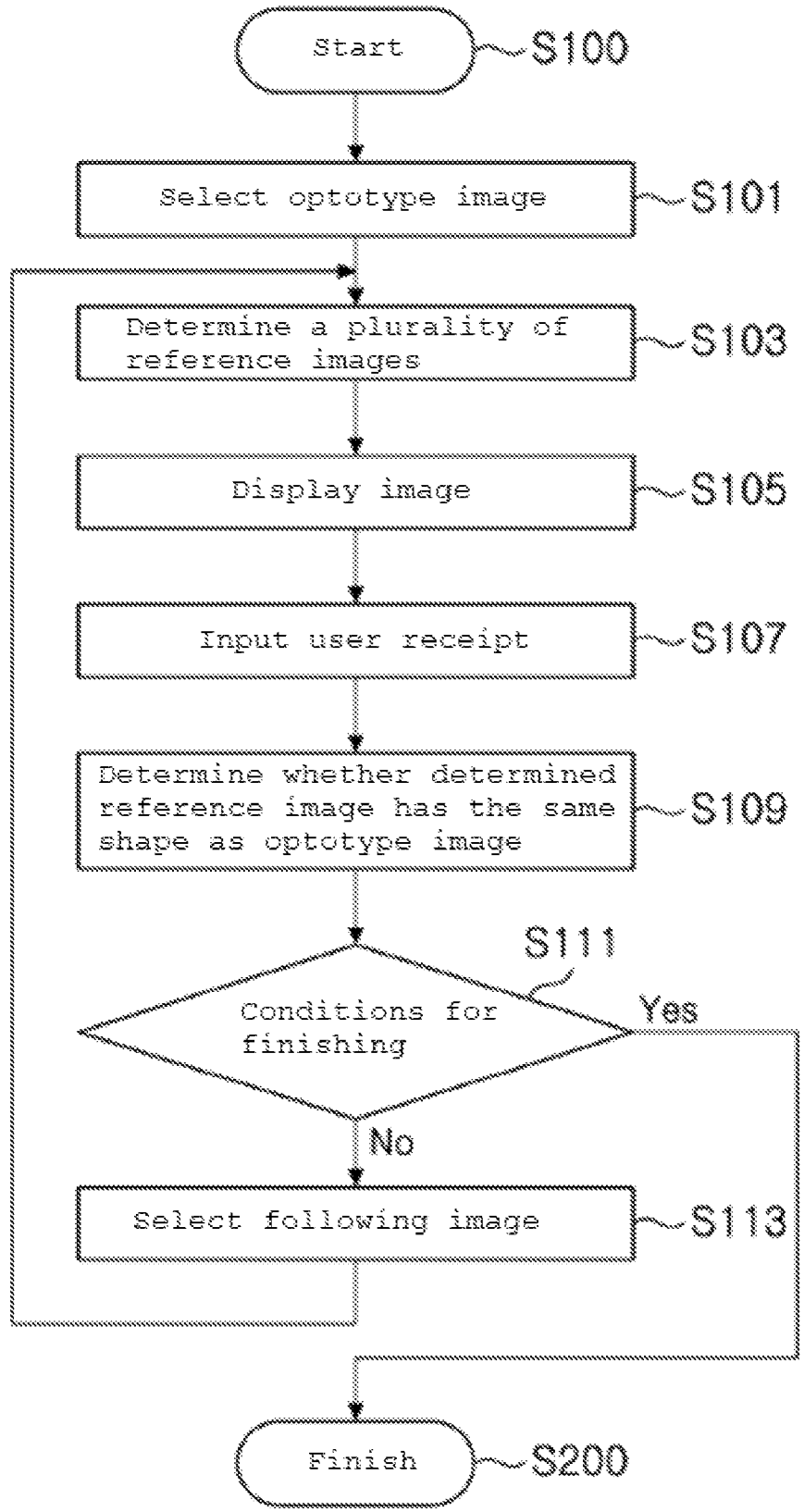
FIG. 6 illustrates an exemplary flow chart of an eyesight examination.
Figure 7:
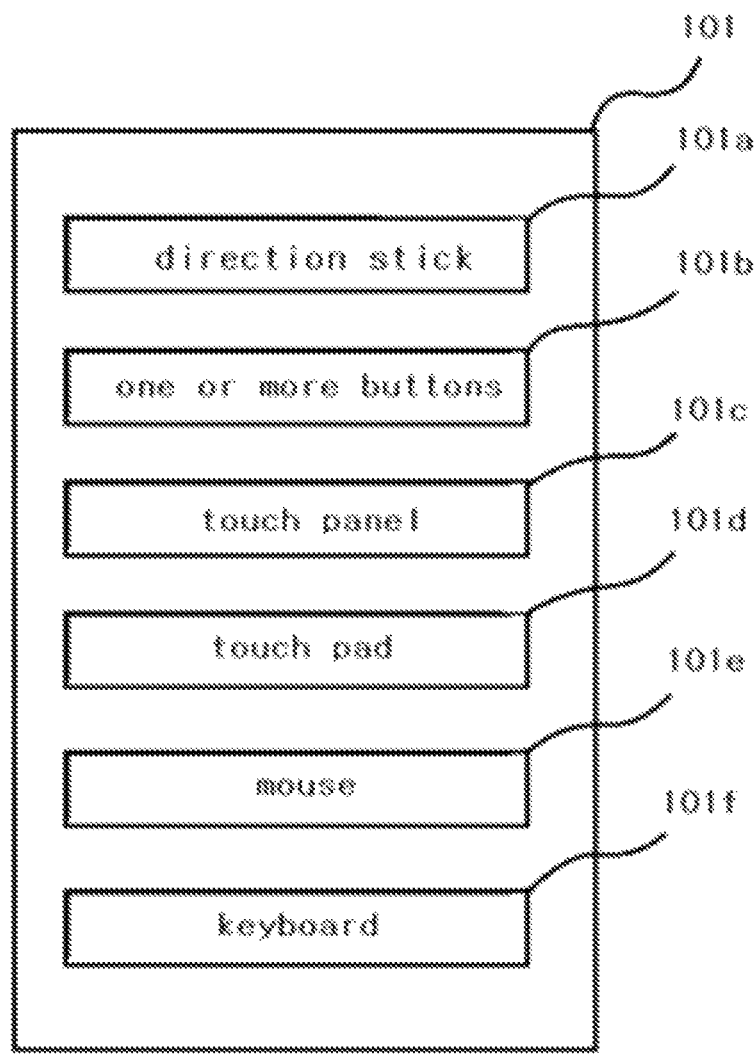
FIG. 7 illustrates an input unit including multiple input devices.

FIG. 6 illustrates an exemplary flow chart of an eyesight examination.

Steps illustrated in the flow chart in FIG. 6 may be performed by an eyesight examination device 100 and preferably performed by controlling other blocks by means of an eyesight examination program loaded by the control unit 117. The eyesight examination program may be a program for various purposes but is at least a program for examining a subject (user)'s eyesight by using an input 101 etc. For instance, the eyesight examination program may be configured such that an eyesight examination is performed like a game during the processes of supplying fairy tale videos or vices to a child. Additionally, the eyesight examination program may be configured such that an eyesight examination is unconsciously performed during a game embedded in a game program supplied to a child or an adolescent etc. As described above, the eyesight examination program may be a program exclusive for an eyesight examination or a program that is embedded in a different kind of program and performs an eyesight examination is performed at a specific time.

The eyesight examination device 100 has been described in detail with reference to FIGS. 1 to 5. Accordingly, repetitive things regarding the eyesight examination device 100 will be briefly described.

First, in a set mode of examining the eyesight of the left eye, the right eye or both eyes, a control unit 117 selects one optotype image among various optotype image groups (S101). For instance, the control unit 117 selects one optotype image group among various optotype image groups consisting of shapes such as a number, a letter, an umbrella, a ship, an airplane etc. and selects one optotype image corresponding to a specific visual acuity value from the selected optotype image group. For instance, the control unit 117 may select an optotype image corresponding to a middle visual acuity value within the range in which an eyesight examination is possible from the optotype image group.

Further, the control unit 117 selects a plurality of reference images (S103). Step 103 may be omitted or performed before step 101 depending on a configuration example of a display unit 111. For instance, if a reference optotype board 111-3, capable of being detached from and coupled to a display module 111-1, is used, a reference optotype board 111-3 that will be used in advance by a manager etc. of the eyesight examination device 100 may be coupled to a display module 111-1. Of a plurality of reference images, at least one reference image has the same shape as the selected optotype image. The reference image having the same shape has a size the same as or larger than that of the largest of the optotype images in the selected optotype image group.

The reference images are configured to be larger than the optotype images such that a subject exactly recognizes a reference image (shape). For instance, the reference image is configured to be the same as or larger than an optotype image corresponding to the lowest visual acuity value of 0.1, a value in which an eyesight examination is possible.

Then, the control unit 117 controls the display unit 111 and displays a selected optotype image and a plurality of reference images such that a subject recognizes the selected optotype image and the plurality of reference images (S105). According to a mode of examining the eyesight of the left eye, the right eye, both eyes, the control unit 117 displays an optotype image and a plurality of reference images in a display section for the left eye and displays an optotype image and a plurality of reference images in a display section for the right eye. In a mode of examining the eyesight of both eyes, the control unit 117 displays two identical optotype images and two identical sets of a plurality of reference images onto a display section (module) for the left eye and a display section (module) for the right eye. The plurality of reference images are displayed on the outskirts of the optotype image, and the subject may determine the direction of each reference image from the optotype image.

The control unit 117 may perform control differently so as to control an optotype image and a plurality of reference images depending on the configuration of the display unit 111.

If the display unit 111 consists of a single graphic pixel-type display module 111-1, the control unit 117 constitutes an image frame by using pixel data of an optotype image and pixel data of a plurality of selected reference images from a storage unit 103, and outputs video signals of the constituted image frame into the single display module 111-1. At the time of examining the eyesight of both eyes, two identical optotype images and two identical sets of reference images are displayed on the image frame, and at the time of examining the eyesight of one eye (the heft eye or the right eye), a single optotype image and a plurality of reference images positioned on the outskirts of the optotype image are displayed onto the image frame in the relevant display section.

If the display unit 111 consists of two graphic pixel-type display modules 111-1, the control unit 117 constitutes image frames for display modules 111-1 corresponding according to modes of examining the eyesight of one eye or both eyes, and outputs video signals of the constituted image frames into the relevant display module 111-1. The control unit 117 may constitutes one or two image frames, and each image frame includes an optotype image and may further include a plurality of reference images. If a reference optotype board 111-3 is coupled to the display unit 111, a plurality of reference images are not included in an image frame, and the control unit 117 may turn on one or more LED corresponding to a plurality of reference images by controlling a lighting unit 113 so as to display the plurality of reference images of the reference optotype board 111-3.

If the display unit 111 consists of a segment-type display modules 111-1, the control unit 117 outputs control signals into one or two display modules 111-1 so as to display a selected optotype image (e.g. highlighting the relevant optotype image or supplying lighting etc.). Further, the control unit 117 may turn on one or more LEDs corresponding to one or two sets of reference images selected according to an eyesight examination mode among two sets of reference images by controlling the lighting unit 113 so as to display each of the plurality of reference images of the reference optotype board 111-3. The LED may output a light source onto a corresponding reference image. Accordingly a subject may recognize a marked reference image.

Regardless of the type of the display unit 111, displayed reference images are all positioned on the outskirts of displayed optotype images. That is, reference images are positioned on the outskirts of various directions selected in connection with a direction stick or output button (e.g. button for selecting upward, downward, left and right directions) of an input unit 101. Each of the reference images is positioned on the outskirts of an optotype image in different directions.

As described above, the control unit 117 displays an optotype image and a plurality of reference images, and a subject may recognize such images. Accordingly, a user inputs a response to the displayed optotype image through the input unit 101, and the control unit 117 receives the user's response representing the response to the optotype image through the input unit 101 (S107).

Then, according to the receipt of the user's response representing the response to the optotype image, the control unit 117 determines a reference image selected from the plurality of displayed reference images on the basis of the response and determines whether the determined reference image has the same shape as the optotype image that is currently displayed (S109). The response is a user input representing a selection of a reference image having the same shape as the optotype image. Only one reference image among a plurality of reference images has the same shape as the optotype image that is currently displayed so as to induce the subject to make an exact selection.

Take a closer look at this with reference to examples. The subject recognizes the optotype image through the eyes and also recognizes a plurality of images positioned on the outskirts of the optotype image. The subject may recognize a reference image having the same shape as an optotype image by comparing each of the plurality of reference images with optotype images. The subject may supply a user input for selecting a reference image recognized as having the same shape as an optotype image through the input unit 101 through the input unit 101 so as to show a recognized reference image. For instance, the subject may input, into the input unit 101, a response including a direction input for showing the relevant direction by using the direction stick etc. so as to select an identical reference image positioned on the outskirts of the optotype image in direction 2, direction 4, direction 8 etc.

According to the receipt of the direction input of the response, the control unit 117 receives a direction input through the input unit 101, determines a reference image corresponding to the direction input among a plurality of reference images and determines whether the corresponding reference image has the same shape as the optotype image that is currently displayed. For instance, in the state where the control unit determines a direction value of a reference image with an identical shape in advance (at S103 or S105), the control unit 117 may determine whether a reference image of the direction input selected by the subject is the same as the optotype image that is currently displayed by comparing the determined direction value with the received direction value.

Then, the control unit 117 determines a condition for finishing the eyesight examination (S111). The condition for finishing the eyesight examination may be frequencies of displaying optotype images repetitively (S105), the question of whether results of an eyesight examination are precise according to user inputs etc. If results of an eyesight examination are precise, the control unit 117 may output the results of the eyesight examination through an output unit 107 or an external interface unit 105.

If the condition for finishing the eyesight examination is satisfied, step 200 is performed, and the control unit 117 finishes the steps of the flow chart in FIG. 6.

If the condition for finishing the eyesight examination is not satisfied, the control unit 117 selects an optotype image (S113), which will be displayed, according to the earlier receipt of the above-described response and the determination. If the control unit determined earlier (S109) that a reference image has the same shape as an optotype image, the control unit 117 selects a smaller optotype image corresponding to a visual acuity value (e.g. 1.2) higher than that corresponding to the optotype image that was displayed earlier (e.g. 1.0). If the control unit determined earlier (S109) that a reference image was not the same as an optotype image, the control unit 117 selects a larger optotype image corresponding to a visual acuity value (e.g. 0.8) lower than that corresponding to the optotype image that was displayed earlier (e.g. 1.0).

According to a selection of a following optotype image, the control unit 117 repetitively performs steps S103 to S109 so as to precisely perform an eyesight examination with respect to the subject. At step 105, the control unit 117 may display a following optotype image and a plurality of reference images used to select the following optotype image.

As described above, according to an eyesight examination method of the present invention, an eyesight examination may be performed with a user input showing that reference images recognized by a subject and an optotype image are the same. Additionally, an eyesight examination is performed with a direction input for selecting a reference image around an optotype image, and by doing so, anyone can perform an eyesight examination readily. Further, an eyesight examination according to the present invention is similar to a game of finding pictures with the same shape. Accordingly, an eyesight examination according to the present invention may provide fun to subjects and may be linked with other games or contents such that an eyesight examination is performed while other games or contents are played.

The present invention with the above-described configuration is capable of performing an eyesight examination in an exact way regardless of whether a subject has astigmatism etc. by using images having a variety of shapes, and is applicable to an eyesight examination for astigmatism etc. An eyesight examination may be performed for various subjects because a subject can simply and intuitively provide input for an eyesight examination through a unified input method to show an image the same as an image comparison of the present invention.

Meanwhile, an eyesight examination program performing the steps of the flow chart in FIG. 6 may be downloaded from a downloader server through a network.

The downloader server includes at least a communication module, a storage module and a control module so as to control the download of a requested program.

The communication module receives a download request through a network such as the Internet etc. and transmits a program corresponding to the download request (e.g. an eyesight examination program) to a device (e.g. an eyesight examination device 100) requesting a download through a network. The communication module includes a chipset for dealing with one or more wire local area networks or wireless local area networks so as to transmit and receive data.

The storage module is provided with a mass storage medium such as a hard disk etc. so as to store a plurality of downloadable programs. The storage module stores an eyesight examination program capable of performing an eyesight examination (ref. FIG. 6) according to at least the present invention.

The control module includes one or more execution units so as to search a program stored in the storage module according to the download request received through the communication module, extracts a requested program and transmits the extracted program to a device requesting a download through the communication module in response to the request.

For instance, the control module extracts an eyesight examination program from the storage module at the request for the download of an eyesight examination program and delivers the extracted eyesight examination program to the communication module so as to transmit the same to an eyesight examination device 100 requesting a download.

An optotype image displayed onto the present invention may be configured as various kinds of images. The optotype image may be configured as a number, a picture or a letter etc. Further, the optotype image may be configured as color vision examination images used for a color amblyopia examination or color blindness examination.

An eyesight examination method and an eyesight examination device 100 of the present invention may perform a color vision examination alternatively, or together with other eyesight examinations by confirming a response through a user input. Optotype images used for a color vision examination consist of dots of different colors, and specific colors represent specific numbers, so as to examine whether a subject recognizes specific colors. If optotype images are ones for an eye vision examination, one of the plurality of displayed reference images represents a number the same as a number expressed as dots having identical colors in an optotype image. For instance, reference images may appear black.

At the time of testing color vision, two display modules 111-1 or a single display module 111-1 may be used in a method for examining eyesight and for an eyesight examination device 100, and one eye or both eyes may be displayed in black.

INDUSTRIAL APPLICABILITY

The present invention that has been described above should not be limited to the above-described embodiments and the attached drawings because the present invention may be replaced, modified and changed in various ways without departing from the technical spirit of the present invention by one of ordinary skill in the art to which the present invention pertains.

The invention claimed is:
1. An eyesight examination device comprising:
a display unit including two display modules displaying an optotype image and a plurality of reference images;
an input unit being provided with a direction stick for choosing any of multiple directions, one or more buttons, a touch panel, a touch pad, a mouse, and a keyboard so as to receive a user input showing a response to an optotype image displayed for an eyesight examination; and
a control unit including one or more execution units for executing a program code, one or more execution units including a processor, a microcomputer, a central processing unit (CPU) or a micro processing unit (MPU), and determining whether of the plurality of reference images, a reference image determined through the response has the same shape as the optotype image, wherein:
one reference image among the plurality of reference images has the same shape as the optotype image,
the display unit comprises two display modules consisting of an LCD module or LED module and for displaying each optotype image, and a reference optotype board for respectively displaying a plurality of reference images and for accommodating the two display modules, and
the plurality of reference images are printed on the reference optotype board or expressed through hollow relief or relief.
2. The eyesight examination device according to claim 1, wherein:
each of the plurality of reference images displayed onto the display unit are positioned on the outskirts of the displayed optotype image in different directions,
the response received through the input unit comprises a direction input for selecting one reference image among a plurality of reference images, and
the control unit determines whether of the plurality of reference images, a reference image corresponding to a direction input of the response and the optotype image have the same shape.
3. The eyesight examination device according to claim 1, wherein:
the control unit selects a following optotype image according to a result of determination on a determined reference image and an optotype image, and outputs a selected following optotype image and a plurality of reference images through the display unit, and
the display unit displays two optotype images and two sets of a plurality of reference images positioned respectively on the outskirts of each of the optotype images such that both eyes of a subject are examined.

\* \* \* \* \*